US00PP19238P2

(12) United States Plant Patent
van der Knaap

(10) Patent No.: US PP19,238 P2
(45) Date of Patent: Sep. 16, 2008

(54) ***KALANCHOE* PLANT NAMED 'DON CARLOS'**

(50) Latin Name: *Kalanchoe blossfeldiana*
Varietal Denomination: Don Carlos

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 0 days.

(21) Appl. No.: 11/787,685

(22) Filed: Apr. 16, 2007

(51) Int. Cl.
*A01H 5/00* (2006.01)

(52) U.S. Cl. ..... Plt./340

(58) Field of Classification Search ..... Plt./340
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Kalanchoe* plant named 'Don Carlos', characterized by its upright, uniform and vigorous growth habit; dark green-colored leaves; uniform and freely flowering habit; double orange-colored flowers; and excellent postproduction longevity.

1 Drawing Sheet

Botanical designation: *Kalanchoe blossfeldiana.*
Cultivar denomination: 'Don Carlos'.

BACKGROUND OF THE INVENTION

The present invention relates to a new and distinct cultivar of *Kalanchoe,* botanically known as *Kalanchoe blossfeldiana,* and hereinafter referred to by the name 'Don Carlos'.

The new *Kalanchoe* is a product of a planned breeding program conducted by the Inventor in Naaldwijk, The Netherlands. The objective of the breeding program is to create new double-flowered *Kalanchoe* cultivars with attractive foliage and flower coloration.

The new *Kalanchoe* originated from a cross-pollination made by the Inventor in Naaldwijk, The Netherlands in March, 2004, of a proprietary selection of *Kalanchoe blossfeldiana* identified as code number 20010833-001, not patented, as the female, or seed parent with a proprietary selection of *Kalanchoe blossfeldiana* identified as code number 20010644-001, not patented, as the male, or pollen, parent. The cultivar Don Carlos was discovered and selected by the Inventor as a flowering plant from within the progeny of the stated cross-pollination in a controlled environment in Naaldwijk, The Netherlands in January, 2005.

Asexual reproduction of the new *Kalanchoe* by vegetative terminal cuttings in a controlled environment in Naaldwijk, The Netherlands, has shown that the unique features of this new *Kalanchoe* are stable and reproduced true to type in successive generations.

SUMMARY OF THE INVENTION

The cultivar Don Carlos has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Don Carlos'. These characteristics in combination distinguish 'Don Carlos' as a new and distinct cultivar of *Kalanchoe:*

1. Upright, uniform and vigorous growth habit.
2. Dark green-colored leaves.
3. Uniform and freely flowering habit.
4. Double orange-colored flowers.
5. Excellent postproduction longevity.

Plants of the new *Kalanchoe* can be compared to plants of the female parent selection. Plants of the new *Kalanchoe* differ from plants of the female parent selection in the following characteristics:

1. Plants of the new *Kalanchoe* have double flowers whereas plants of the female parent selection have single flowers.
2. Plants of the new *Kalanchoe* and the female parent selection differ in flower color as plants of the female parent selection have orange and yellow bi-colored flowers.

Plants of the new *Kalanchoe* can also be compared to plants of the male parent selection. Plants of the new *Kalanchoe* differ primarily from plants of the male parent selection in plant shape and flower color.

Plants of the new *Kalanchoe* can be compared to plants of the *Kalanchoe blossfeldiana* cultivar Don Juan, disclosed in U.S. Plant Pat. No. 17,576. In side-by-side comparisons conducted in Naaldwijk, The Netherlands, plants of the new *Kalanchoe* differed from plants of the cultivar Don Juan in the following characteristics:

1. Plants of the new *Kalanchoe* were slightly larger than plants of the cultivar Don Juan.
2. Flowers of plants of the new *Kalanchoe* were orange in color whereas flowers of plants of the cultivar Don Juan were red in color.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe*.

The photograph at the top of the sheet comprises a side perspective view of a typical flowering plant of 'Don Carlos' grown in a container.

The photograph at the bottom of the sheet comprises a top perspective view of a typical flowering plant of 'Don Carlos'.

DETAILED BOTANICAL DESCRIPTION

The aforementioned photographs and following observations, measurements and values describe plants grown in Naaldwijk, The Netherlands in a glass-covered greenhouse during the winter and under conditions which closely approximate commercial production. During the production of the plants, day temperatures were about 20° C. to 22° C., night temperatures were about 18° C. to 20° C. and light levels ranged from about 5 kilolux to 60 kilolux. Plants grown in 12-cm containers received long day/short night conditions (more than 14 hours of light) for about five weeks; plants then received photoinductive short day/long night conditions (minimum 14 hours darkness) until flowering. Plants were about 14 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* cultivar Don Carlos.

Parentage:

*Female, or seed, parent.*—Proprietary selection of *Kalanchoe blossfeldiana* identified as code number 20010833-001, not patented.

*Male, or pollen parent.*—Proprietary selection of *Kalanchoe blossfeldiana* identified as code number 20010644-001, not patented.

Propagation:

*Type.*—By vegetative terminal cuttings.

*Time to initiate roots, summer.*—About ten days at temperatures of 21° C.

*Time to initiate roots, winter.*—About two weeks at temperatures of 21° C.

*Time to produce a rooted young plant, summer.*—About three weeks at temperatures of 21° C.

*Time to produce a rooted young plant, winter.*—About four weeks at temperatures of 21° C.

*Root description.*—Fine, fibrous; white in color.

*Rooting habit.*—Freely branching.

Plant description:

*Plant habit.*—Upright, uniform and vigorous growth habit. Very freely flowering with numerous compound cymes. Inverted triangle with rounded crown. Appropriate for 10-cm to 13-cm containers.

*Plant height at flowering.*—About 17 cm.

*Plant diameter at flowering.*—About 31 cm.

Lateral branch description:

*Branching habit.*—Freely branching habit; usually about ten lateral branches develop per plant.

*Length.*—About 14 cm to 16 cm.

*Diameter.*—About 1 cm.

*Internode length.*—About 1 cm to 1.5 cm.

*Aspect.*—Erect.

*Strength.*—Strong.

*Texture.*—Smooth, glabrous.

*Color.*—Close to 146A.

Foliage description:

*Arrangement.*—Opposite, simple; generally symmetrical. Length, generative plants: About 6 cm to 15 cm. Width, generative plants: About 4.5 cm to 10.5 cm.

*Shape.*—Ovate.

*Apex.*—Rounded.

*Base.*—Obtuse.

*Margin.*—Crenate; undulate.

*Texture, upper and lower surfaces.*—Glabrous, leathery; succulent.

*Venation pattern.*—Pinnate; reticulate.

*Color.*—Developing foliage, upper surface: Close to 137A to 137B. Developing foliage, lower surface: Close to 146A. Fully expanded foliage, upper surface: Close to 147A; venation, close to 146A to 146B. Fully expanded foliage, lower surface: Close to 146A; venation, 146A.

*Petiole.*—Length: About 1 cm to 2 cm. Diameter: About 7 mm to 10 mm. Texture, upper and lower surfaces: Smooth, glabrous. Color, upper and lower surfaces: Close to 144B.

Flower description:

*Flower arrangement and habit.*—Double flowers arranged singly in compound dichasial cymes that arise from leaf axils. Uniform and freely flowering habit with usually about 24 to 30 flowers developing per inflorescence. Flowers persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long conditions (at least 14 hours of darkness).

*Time to flower.*—Under short day/long night photoinductive conditions, about 70 days are required. Actual time to flower is primarily dependent upon temperature and light intensity.

*Post-production longevity.*—Excellent post-production longevity; flowers maintain good substance for about four weeks under interior environmental conditions.

*Inflorescence height.*—About 4 cm to 5 cm.

*Inflorescence diameter.*—About 6 cm to 10 cm.

*Flower diameter.*—About 1.8 cm.

*Flower length (height).*—About 1.3 cm to 1.5 cm.

*Flower bud.*—Shape: Ovoid. Length: About 6 mm to 7 mm. Diameter: About 4 mm. Color: Close to 43D.

*Petals.*—Arrangement: About 25 fused at the base. Length (largest petals): About 1.4 cm. Width (largest petals): About 7 mm. Aspect: Slightly upright to eventually recurved. Shape: Spatulate. Apex: Apiculate. Margin: Entire. Texture, upper and lower surfaces: Smooth, glabrous; satiny. Color: When opening, upper surface: Close to 45B. When opening, lower surface: Between 43D and 39B. Fully opened, upper surface: Close to 33A; color becoming closer to 41A with development. Fully opened, lower surface: Between 43D and 52C.

*Sepals.*—Appearance: Four fused at the base. Length: About 7 mm. Width: About 3 mm. Shape: Lanceolate. Apex: Acute. Margin: Entire. Texture, upper and lower surfaces: Smooth; glabrous. Color, upper and lower surfaces: 144A.

*Peduncles.*—Length: About 9 cm to 11 cm. Diameter: About 3 mm to 5 mm. Aspect: Mostly erect. Strength: Moderately strong. Texture: Smooth, glabrous. Color: Close to 146B.

*Pedicels.*—Length: About 2 mm to 3 mm. Diameter: About 2 mm to 2.5 mm. Aspect: Erect to about 90° from vertical. Strength: Moderately strong. Texture: Smooth, glabrous. Color: Close to 146A.

*Reproductive organs.*—Androecium: Stamen number: About six per flower. Anther shape: Deltoid; base, sagittate. Anther length: About 0.3 mm. Anther color: Close to 22A. Amount of pollen: None observed. Gynoecium: Pistil number: About five per flower. Pistil length: About 9 mm. Style length: About 2 mm to 3 mm. Style color: Close to 145C. Stigma shape: Rounded. Stigma color: Close to 154D. Ovary color: Close to 145A.

*Seed/fruit.*—Seed and fruit development have not been observed.

Temperature tolerance: Plants of the new *Kalanchoe* have been observed to tolerate temperatures from about 5° C. to about 35° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Don Carlos' as illustrated and described.

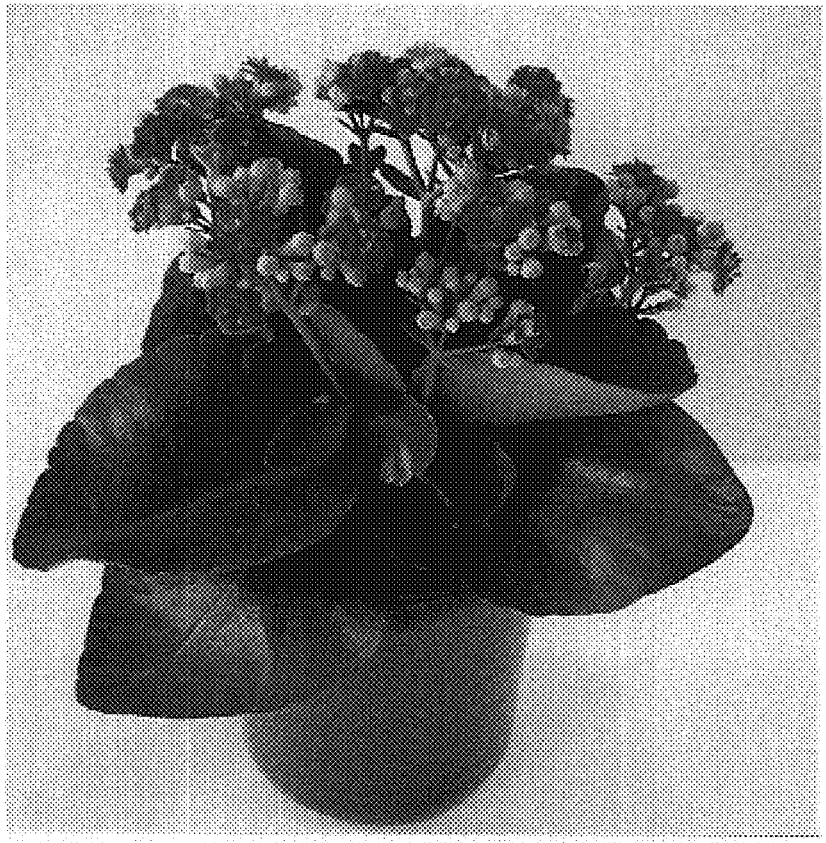
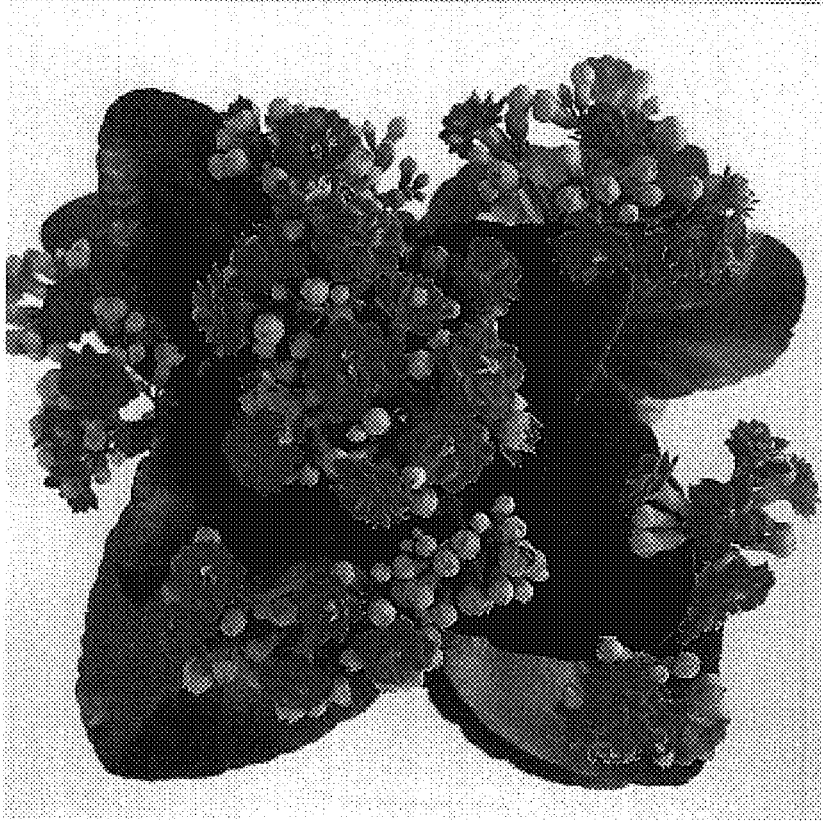

* * * * *